(12) United States Patent
Kawaguchi et al.

(10) Patent No.: US 8,350,877 B2
(45) Date of Patent: Jan. 8, 2013

(54) PRINT STATE DETECTING DEVICE FOR PRINTED SHEET SURFACE, ERASING APPARATUS, AND PRINT STATE DETECTION METHOD FOR PRINTED SHEET SURFACE

(75) Inventors: Takahiro Kawaguchi, Shizuoka-ken (JP); Isao Yahata, Shizuoka-ken (JP); Ken Iguchi, Shizuoka-ken (JP); Hiroyuki Taguchi, Shizuoka-ken (JP); Hiroyuki Tsuchihashi, Shizuoka-ken (JP); Hiroyuki Taki, Shizuoka-ken (JP)

(73) Assignees: Kabushiki Kaisha Toshiba, Tokyo (JP); Toshiba Tec Kabushiki Kaisha, Tokyo (JP)

( * ) Notice: Subject to any disclaimer, the term of this patent is extended or adjusted under 35 U.S.C. 154(b) by 122 days.

(21) Appl. No.: 13/042,147

(22) Filed: Mar. 7, 2011

(65) Prior Publication Data

US 2011/0221851 A1 Sep. 15, 2011

Related U.S. Application Data

(60) Provisional application No. 61/312,075, filed on Mar. 9, 2010.

(51) Int. Cl.
*B41J 29/16* (2006.01)
(52) U.S. Cl. ......................................... 347/179

(58) Field of Classification Search .................. 347/179, 347/171, 223, 104, 105; 400/120.01; 399/4, 399/186; 250/316.1, 317.1
See application file for complete search history.

(56) References Cited

U.S. PATENT DOCUMENTS

| 5,231,505 A | * | 7/1993 | Watanabe et al. | 347/179 |
| 5,376,951 A | * | 12/1994 | Inoue et al. | 347/179 |
| 5,529,408 A | * | 6/1996 | Moriguchi et al. | 347/179 |
| 6,860,658 B2 | * | 3/2005 | Tischer | 347/179 |

* cited by examiner

*Primary Examiner* — Kristal Feggins
(74) *Attorney, Agent, or Firm* — Patterson & Sheridan, LLP

(57) ABSTRACT

There is provided a print state detection device for a printed sheet surface including a sheet conveying path on which a sheet printed with an image is conveyed, a contact member that contacts with the surface of the sheet moving on the sheet conveying path, a contact state detecting part that detects a physical phenomenon occurring when the contact member contacts with the sheet, a separating part that separates the difference in the physical phenomenon occurring when the contact member comes into contact with the ground of the sheet surface and when the contact member comes into contact with an image, based on detection information obtained by the detection of the contact state detecting part, and a print state determining part that determines the print state of an image on one sheet based on separation information obtained by the separation by the separating part.

20 Claims, 5 Drawing Sheets

PRINT STATE DETECTING DEVICE FOR PRINTED SHEET SURFACE, ERASING APPARATUS, AND PRINT STATE DETECTION METHOD FOR PRINTED SHEET SURFACE

CROSS-REFERENCE TO RELATED APPLICATION

This application is based upon and claims the benefit of priority from: US provisional application, 61/312,075, filed on Mar. 9, 2010; the entire contents of each of which are incorporated herein by reference.

FIELD

The embodiment described in this specification relates to a technology for detecting the print state of a sheet before a decoloring image formed on the sheet is erased.

BACKGROUND

Conventionally, an erasing apparatus which erases a decoloring image printed on a sheet through heating with a print image erasing unit to re-use the sheet is suggested. The print image erasing unit heats the sheet over its entire length in the width and length directions.

In other words, the print image erasing unit consumes heating energy to erase the image over the entire surface of the sheet.

For this reason, even if characters are printed over the entire surface of a sheet, an erasing process is performed with the same heating energy regardless of the value a print ratio that represents the proportion of characters occupying the whole sheet.

In addition, even when images are scattered in a portion of a sheet, other portions with no images are heated.

Thus, a technology wherein the printed surface of a sheet before an erasing process is read by a scanner and the state of the printed surface is detected based on the read image is suggested.

However, a method in which the print state of a sheet is optically detected as with a scanner or the like requires a high cost, and it is difficult to reduce the size of the erasing apparatus of the method in that space to install the optical system is needed.

DETAILED DESCRIPTION

A print state detection device for printed sheet surface according to an embodiment of the invention, as an aspect, includes a sheet conveying path on which a sheet printed with an image is conveyed, a contact member that contacts with the surface of the sheet moving on the sheet conveying path, a contact state detecting part that detects a physical phenomenon occurring when the contact member contacts with the sheet, a separating part that separates the difference in physical phenomenon occurring when the contact member comes into contact with the ground of the sheet surface and when the contact member comes into contact with an image, based on detection information obtained by the detection of the contact state detecting part, and a print state determining part that determines the print state of an image on one sheet based on separation information obtained by the separation by the separating part.

An erasing apparatus according to an embodiment of the invention, as an aspect, includes a sheet conveying path on which a sheet is conveyed, an image erasing part that erases a decoloring image on a sheet moving on the sheet conveying path, a contact member that contacts with the surface of the sheet moving on the sheet conveying path, a contact state detecting part that detects a physical phenomenon occurring when the contact member contacts with the sheet, a separating part that separates the difference in the physical phenomenon occurring when the contact member comes into contact with the ground of the sheet surface and when the contact member comes into contact with an image, based on detection information obtained by the detection of the contact state detecting part, and a print state determining part that determines the print state of an image on one sheet based on separation information obtained by the separation by the separating part.

A print state detection method for printed sheet surface according to an embodiment of the invention, as an aspect, includes moving a sheet printed with an image along a sheet conveying path, bringing a contact member into contact with the surface of the sheet moving on the sheet conveying path, detecting a physical phenomenon occurring when the contact member contacts with the sheet by a contact state detecting part, separating a difference in the physical phenomenon occurring when the contact member comes into contact with the ground of the sheet surface and when the contact member comes into contact with an image, based on detection information obtained by the detection of the contact state detecting part, and determining the printed state of an image on one sheet based on separation information obtained by the separation.

Hereinafter, an embodiment of an erasing apparatus provided with a print state detecting device for a printed sheet surface according to the embodiment will be described with reference to drawings.

Figure 1:
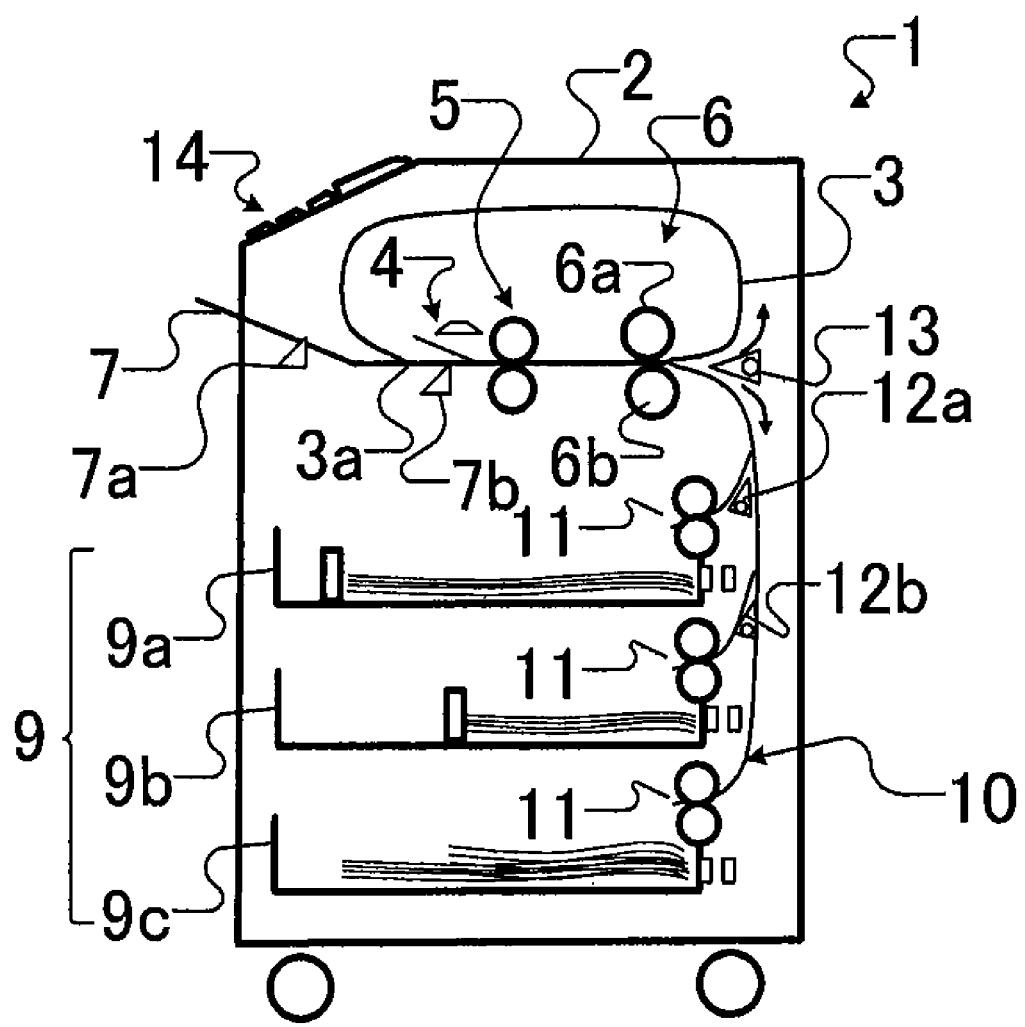
FIG. 1 is a schematic vertical cross-sectional diagram showing an embodiment of an erasing apparatus provided with a print state detecting device for a printed sheet surface.
Figure 2:
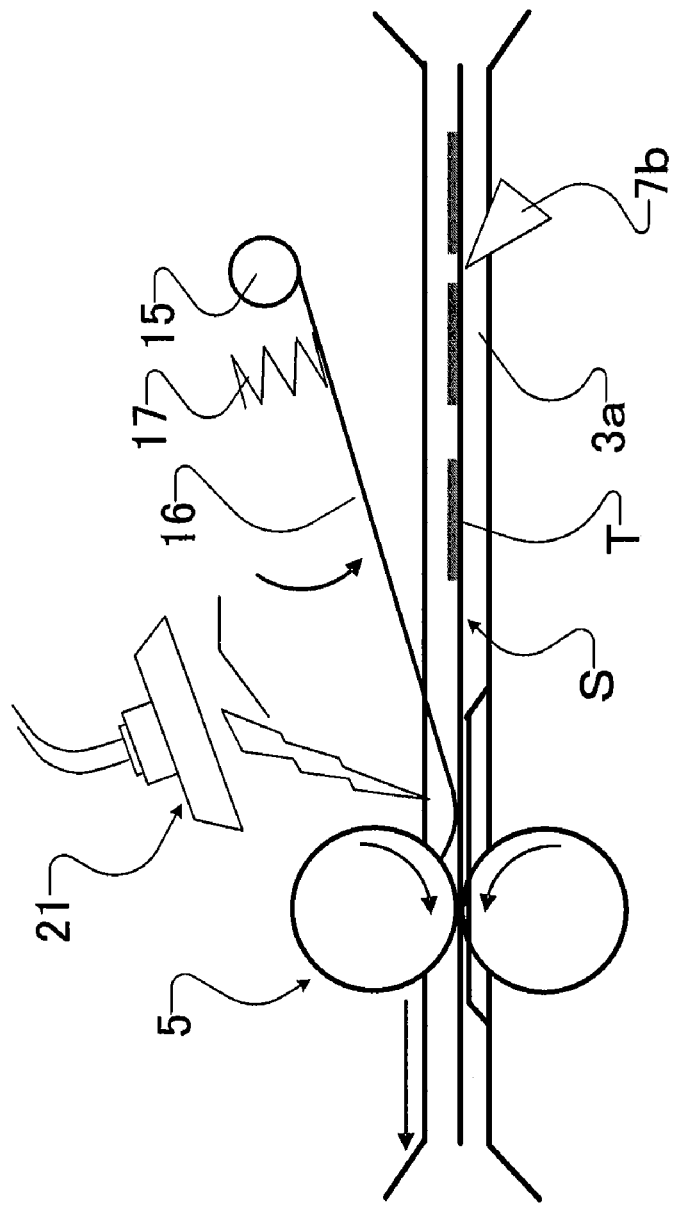
FIG. 2 is a schematic front diagram of the print state detecting device of FIG. 1 showing a state where the terminal end of a conveying guide directly contacts with the surface of a sheet.
Figure 3:
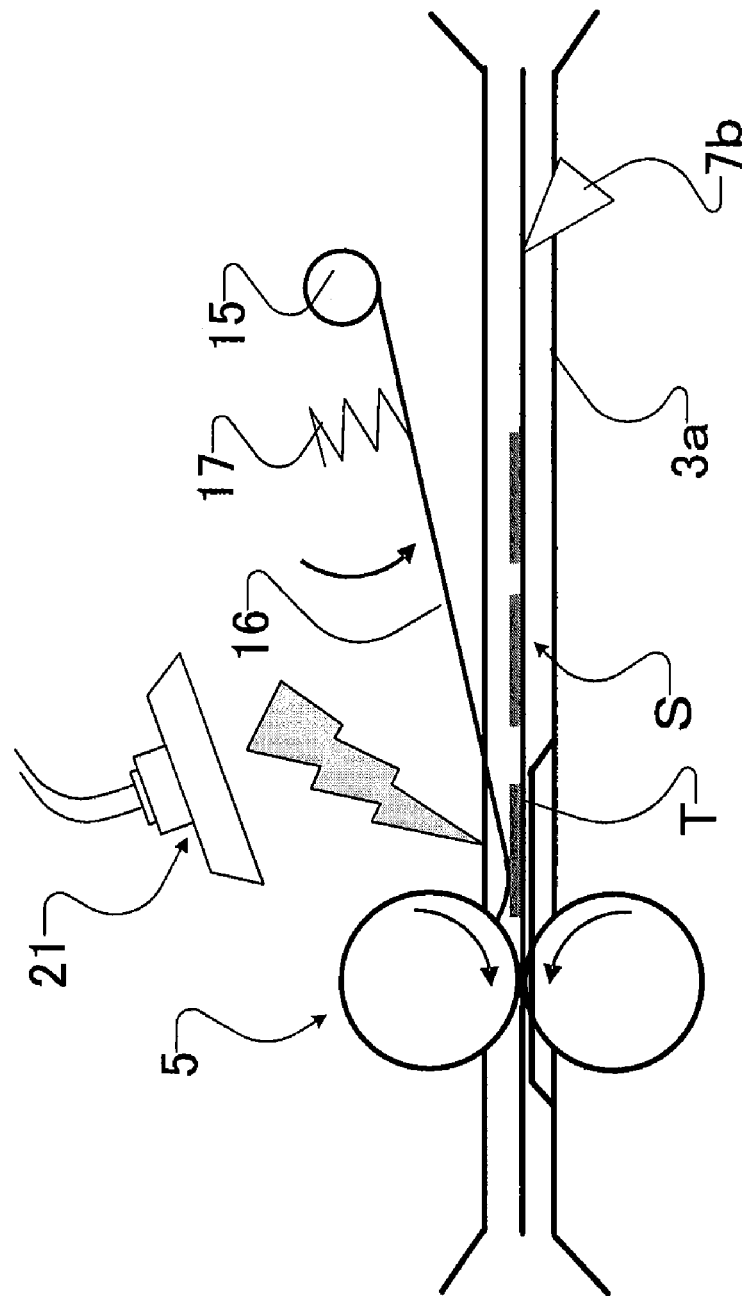
FIG. 3 is a schematic front diagram of the print state detecting device of FIG. 1 showing a state where the terminal end of the conveying guide directly contacts with a printed image on the sheet.
Figure 4:
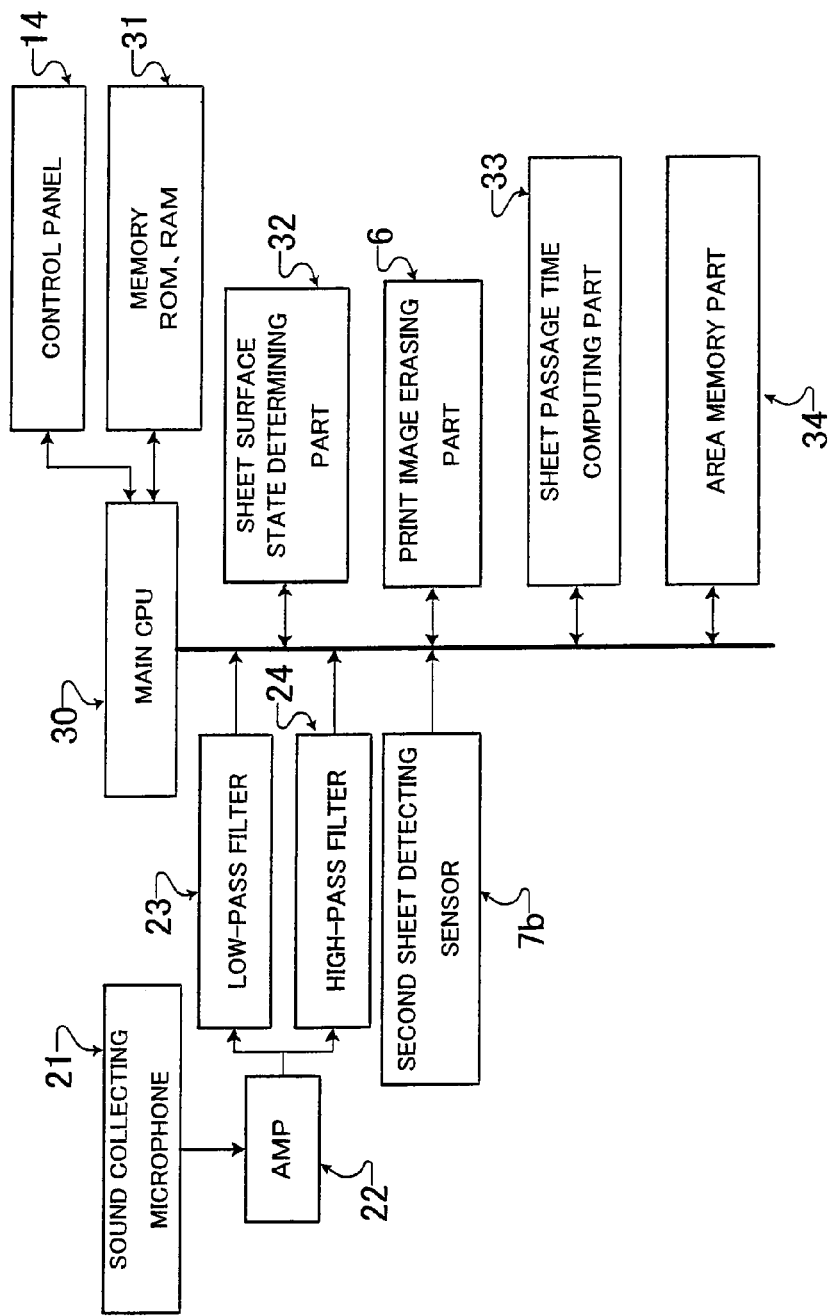
FIG. 4 is a block diagram of a sheet surface state determination circuit of the erasing apparatus of FIG. 1.

FIG. 1 is a schematic vertical cross-section diagram showing an embodiment of the erasing apparatus provided with the print state detecting device for a printed sheet surface, FIG. 2 is a schematic front diagram of the print state detecting device of FIG. 1 showing a state where the terminal end of a conveying guide directly contacts with the surface of a sheet. FIG. 3 is a schematic front diagram of the print state detecting device of FIG. 1 showing a state where the terminal end of the conveying guide directly contacts with a printed image on the sheet. FIG. 4 is a block diagram of a sheet surface state determination circuit of the erasing apparatus of FIG. 1.

The erasing apparatus 1 shown in FIG. 1 has an endless sheet re-conveying path 3 in the upper portion of a housing 2, and a horizontal conveying part 3a in the lower portion is arranged with a detecting part 4, a pair of conveying rollers 5, a print image erasing part 6 of a print state detecting device toward the downstream side from the upstream side of the conveying direction.

The print image erasing part 6 is composed of a pair of upper and lower heating rollers 6a and 6b, and if a pre-erasure sheet passes through a nip portion of the pair of heating rollers 6a and 6b, a decoloring image is erased. In this embodiment, erasing of a decoloring image is performed for both sides of a pre-erasure sheet at the same time. A plurality of heating sources is arranged in the heating rollers 6a and 6b in the longitudinal direction, and power distribution is controlled for each of the heating sources.

There is provided a sheet input tray 7 on which sheets printed with a decoloring image (hereinafter, referred to as pre-erasure sheets) are stacked in the front side of the housing 2. The terminal end of the sheet input tray 7 is arranged in the upper stream end of the horizontal conveying part 3a, and pre-erasure sheets stacked on the sheet input tray 7 are intermittently supplied to the pair of conveying rollers 5 by a pair of sheet feeding rollers not shown in the drawings. Furthermore, a first sheet detecting sensor 7a is provided in the sheet input tray 7 to send a signal of the presence or non-presence of a sheet to a main CPU 30 that controls the entire apparatus shown in FIG. 4. If a signal of sheet presence is output from the sheet detecting sensor 7a, for example, erasing processes are consecutively performed.

In addition, a second sheet detecting sensor 7b is provided in the upper stream side of the pair of conveying rollers 5, and if the sensor detects passage of the leading end of a conveyed sheet S, an ON signal is output to the main CPU 30. If the sensor detects the passage of the tailing end of the sheet S, an OFF signal is output to the main CPU 30. A sheet passage time computing part 33 calculates the passage time of one sheet S based on the detection with ON and OFF signals of the second sheet detecting sensor 7b.

A flapper 13 that switches the conveying direction is arranged facing the conveyance tailing end of the horizontal conveying part 3a. After the switching by the flapper 13, an erasing-completed sheet, that is, a sheet which is not yet determined to be reusable to be described later (hereinafter, referred to as a non-determined sheet) is conveyed to the sheet re-conveying path 3, and an erasing-completed sheet, that is, a sheet which is determined to be reusable (hereinafter, referred to as a determination-completed sheet) is conveyed to a sheet conveying part 10 to be described later.

In the embodiment, a sheet that passed the detecting part 4 and is completed with print state detection passes the print image erasing part 6, and a decoloring image is erased with heat. Furthermore, a large size sheet, such as A3 sheet or the like, runs once around the sheet re-conveying path 3 and is conveyed to the print image erasing part 6.

Below the sheet re-conveying path 3, there is arranged a sheet piling part 9 that piles erasing-completed sheets, that is, sheets that are determined to be reused (hereinafter, referred to as a determination-completed sheet). In the embodiment, the sheet piling part 9 is provided with a cassette mounting part arranged with a plurality of sheet cassettes 9a, 9b, and 9c along the upward and downward directions, and each sheet cassette is configured to be removable from the upper cassette mounting part, the middle cassette mounting part, and the lower cassette mounting part.

The sheet conveying part 10 that conveys determination-completed sheets in the upward and downward directions from the sheet piling part 9 is arranged in the inner portion of the housing 2. The sheet conveying part 10 is provided with a first branched conveying part 10a corresponding to the first sheet cassette 9a, and a second branched conveying part 10b corresponding to the second sheet cassette 9b, and a conveyance end of the sheet conveying part 10 corresponds to the third sheet cassette 9c. In addition, pairs of sheet feeding rollers 11 are arranged in each of the conveyance end of the first branched conveying part 10a, the conveyance end of the second branched conveying part 10b, and the conveyance end of the sheet conveying part 10.

Furthermore, there are arranged sorting devices 12a and 12b corresponding to the first branched conveying part 10a and the second branched conveying part 10b in the sheet conveying part 10. If a determination-completed sheet moving the sheet conveying part 10 arrives at the position of the corresponding sorting device, the sorting device blocks the conveying path of the sheet conveying part 10, the determination-completed sheet is diverged to the branched conveying part, and fed to and accommodated in the corresponding sheet cassette by the pair of sheet feeding rollers 11.

In the embodiment, a determination-completed sheet that is determined to be reusable is accommodated in a sheet cassette of a corresponding size by the drive of the first sorting device 12a and the second sorting device 12b. In addition, a determination-completed sheet that is determined not to be reusable is conveyed from the conveyance end of the sheet conveying part 10 to the third sheet cassette 9c to be accommodated therein without driving of the sorting devices 12a and 12b.

There is provided a control panel 14 provided with a display screen and operation switches on the upper surface of the housing 2.

A detecting part 4 is provided with a plate-shaped conveyance guide 16 that is a contact member coming into contact with the surface of the sheet S conveyed on the horizontal conveying path 3a, and causes the sheet S to be straightly conveyed on the horizontal conveying path 3a. In the embodiment, the conveyance guides 16 are arranged in plural in the main scanning direction orthogonal to the sheet conveying direction, and above a terminal end of each of the conveyance guides, a sound collecting microphone 21 that is a contact state detecting part is arranged.

The conveyance guide 16 can rotate in the upward and downward directions with a support shaft 15 as a fulcrum, and spring force of a spring 17 causes the terminal end of the conveyance guide 16 to come into gentle contact with the surface of the sheet S.

If, for example, an image T is formed on the surface of the sheet T with a toner, and the terminal end of the conveyance guide 16 contacts with the image T as shown in FIG. 3 as the sheet S moves in the downstream side of the conveying direction, a friction sound becomes low due to the friction contact with the image T having a small friction coefficient. On the contrary, the terminal end of the conveyance guide 16 directly contacts with a non-image-formed portion where the image T is not formed on the sheet surface as shown in FIG. 2, a high friction contact sound is generated.

The sound collecting microphone 21 collects sound made when the terminal end of the conveyance guide 16 contacts with the sheet S.

In the block diagram of the sheet surface state determination circuit shown in FIG. 4, the main CPU 30 downloads a program stored in a ROM of memory 31 to operate a sheet surface state determination process. If the sheet surface state determination process is selected by an instruction of the control panel 14, the contact sound generated between the sheet S and the terminal end of the conveyance guide 16 and collected by the sound collecting microphone 21 is amplified in an amplifier 22. The contact sound amplified in the amplifier 22 passes through a low-pass filter 23 and a high-pass filter 24, and is separated into a low contact sound and a high contact sound.

The sheet passage time computing part 33 calculates the overall length of the sheet S based on the passage time of the sheet S conveyed at a constant speed to determine the size of the sheet S.

When the second sheet detecting sensor 7b detects the leading end of the sheet S, the sheet surface state determination part 32 detects low sound information from the low-pass filter 23 and high sound information from the high-pass filter 24 with the passage of time after the time when the leading end of the sheet S arrives at the terminal end of the conveyance guide 16 passes, and stores the information in an area memory part 34. In other words, an area where the image T serving as the generation source of the low sound information in the sheet conveying direction is present is presumed and stored in the area memory part 34. In this case, the area is the width of the conveyance guide 16 in the main scanning direction.

The sheet surface state determination part 32 obtains the total low sound area and the total high sound area for one sheet S and a print rate is obtained based on the rates of the areas. Furthermore, the print rate may be obtained from the ratio of the area of the total low sound to the area of the sheet S.

In addition, an image T presence area and an image T non-presence area in the sheet S in the conveying direction can be presumed for the conveyance guide 16.

Therefore, electric power supplied to the heat source of the print image erasing part 6 can be adjusted according to the print rate and power save can be intended by heating only the image T presence area.

Figure 5:
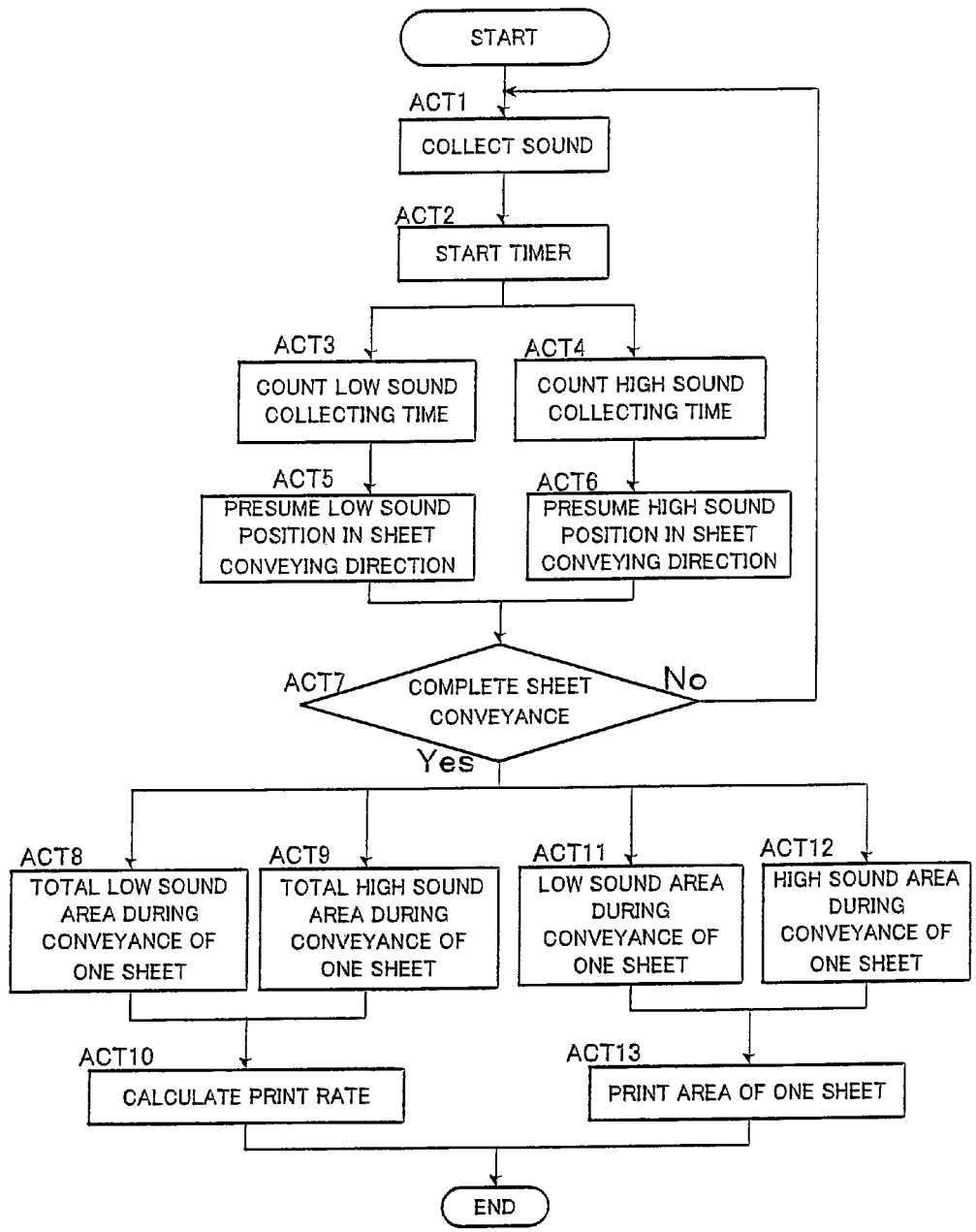
FIG. 5 is a flowchart illustrating a print rate determining operation and a print area determining operation of the sheet surface state determination part of FIG. 4.

FIG. 5 shows a flowchart of print rate determination and print area determination.

In FIG. 5, the sound collecting microphone 21 collects friction sounds generated when the conveyance guide 16 contacts with the sheet S (ACT 1). A timer starts after the sheet S starts to contact with the terminal end of the conveyance guide 16 (ACT 2), and when low sounds are collected, a low sound collecting time is counted (ACT 3). In addition, when high sounds are collected, a high sound collecting time is counted (ACT 4).

In ACT 5, a low sound position in the sheet conveying direction is presumed based on the time when low sounds are collected, and in ACT 6, a high sound position in the sheet conveying direction is presumed based on the time when high sounds are collected.

The process from ACT 3 to ACT 6 is performed until the conveyance of one sheet is completed (ACT 7).

When the conveyance of the one sheet is completed, the total low sound area during the conveyance of the one sheet is obtained from the low sound position obtained in ACT 5 (ACT 8), the total high sound area during the conveyance of the one sheet is obtained from the high sound position obtained in ACT 6 (ACT 9), and the print rate is obtained from the total low sound area and the total high sound area (ACT 10).

In addition, when the conveyance of the one sheet is completed, each low sound area during the conveyance of the one sheet is obtained from the low sound position obtained in ACT 5 (ACT 11), each high sound area during the conveyance of the one sheet is obtained from the high sound position obtained in ACT 6 (ACT 12), and the printed are on the one sheet is obtained (ACT 13).

In the above-described embodiment, when the contact member contacts gently with the sheet surface moving on the conveying path, a difference occurs in the physical phenomenon generated during the contact between an image portion with low friction having good sliding and the sheet surface with high friction having bad sliding, the contact state detecting part detects the difference to specify the image portion on the sheet, but vibration or the like may be detected as the physical phenomenon in addition to friction contact sounds.

In addition, the above-described embodiment shows a case where a sheet surface state determination device detects a decoloring image formed on a sheet surface, but such detection is not limited to the decoloring image, and possible for an image formed with a color material with a non-decoloring property.

The process described in the embodiment is exemplified for a case where a program stored in advance in the memory 31 provided in the erasing apparatus 1 is executed by the main CPU 30 for processing inner data, but the program may be downloaded in the main CPU through a network, and a program stored in a computer-readable recording medium may be installed in a CPU. As the recording medium, a recording medium that can store programs and be readable by a computer is possible. As such a recording medium, for example, a RAM (Random Access Memory), a ROM (Read Only Memory), a DRAM, an SRAM (Static Random Access Memory), a VRAM (Video RAM), a flash memory can be used.

The present invention can be implemented in various other forms not departing from the gist or important features. For this reason, the above-described embodiment is just a simple example of all points, and cannot be interpreted determinatively. The scope of the invention is shown by claims and not constrained by the specification. Furthermore, all transformations, various improvements, substitutions, and modifications that belong to the same range as the claims are within the scope of the invention.

What is claimed is:

1. A print state detection device for a printed sheet surface comprising:
 a sheet conveying path on which a sheet printed with an image is conveyed;
 a contact member that contacts with the surface of the sheet moving on the sheet conveying path;
 a contact state detecting part that detects a physical phenomenon occurring when the contact member contacts with the sheet;
 a separating part that separates the difference in the physical phenomenon occurring when the contact member comes into contact with the ground of the sheet surface and when the contact member comes into contact with an image, based on detection information obtained by the detection of the contact state detecting part; and
 a print state determining part that determines the print state of an image on one sheet based on separation information obtained by the separation by the separating part.

2. The device according to claim 1, wherein the contact state detecting part is a sound collecting microphone that detects a friction contact sound generated as the physical phenomenon.

3. The device according to claim 1, wherein the contact member is provided in plural in a direction orthogonal to the conveyance direction of a sheet, and the contact state detecting part is provided corresponding to each contact member.

4. The device according to claim 1, wherein a print state determined by the print state determining part is a print rate representing the degree of an image portion occupying the whole sheet.

5. The device according to claim 1, wherein a print state determined by the print state determining part is the area of an image portion in the whole sheet.

6. The device according to claim 1, wherein the contact member is a conveyance guide that contacts with the surface of a sheet and guides the conveyance of the sheet.

7. The device according to claim 6, comprising a spring that biases the conveyance guide to the surface of the sheet.

8. An erasing apparatus comprising:
   a sheet conveying path on which a sheet is conveyed;
   an image erasing part that erases a decoloring image on a sheet moving on the sheet conveying path;
   a contact member that contacts with the surface of the sheet moving on the sheet conveying path;
   a contact state detecting part that detects a physical phenomenon occurring when the contact member contacts with the sheet;
   a separating part that separates the difference in the physical phenomenon occurring when the contact member comes into contact with the ground of the sheet surface and when the contact member comes into contact with an image, based on detection information obtained by the detection of the contact state detecting part; and
   a print state determining part that determines the print state of an image on one sheet based on separation information obtained by the separation by the separating part.

9. The apparatus according to claim 8, wherein the contact state detecting part is a sound collecting microphone that detects a friction contact sound generated as the physical phenomenon.

10. The apparatus according to claim 8, wherein the contact member is provided in plural in a direction orthogonal to the conveyance direction of a sheet, and the contact state detecting part is provided corresponding to each contact member.

11. The apparatus according to claim 8, wherein the print state determined by the print state determining part is a print rate representing the degree of an image portion occupying the whole sheet.

12. The apparatus according to claim 8, wherein the print state determined by the print state determining part is the area of an image portion in the whole sheet.

13. The apparatus according to claim 8, wherein the contact member is a conveyance guide that contacts with the surface of a sheet and guides the conveyance of the sheet.

14. The apparatus according to claim 13, comprising a spring that biases the conveyance guide to the surface of the sheet.

15. A print state detection method for a printed sheet surface comprising:
   moving a sheet printed with an image along a sheet conveying path;
   bringing a contact member into contact with the surface of the sheet moving on the sheet conveying path;
   detecting a physical phenomenon occurring when the contact member contacts with the sheet by a contact state detecting part;
   separating a difference in the physical phenomenon occurring when the contact member comes into contact with the ground of the sheet surface and when the contact member comes into contact with an image, based on detection information obtained by the detection of the contact state detecting part; and
   determining the print state of an image on one sheet based on separation information obtained by the separation.

16. The method according to claim 15, wherein the contact state detecting part is a sound collecting microphone that detects a friction contact sound generated as the physical phenomenon.

17. The method according to claim 16, wherein the contact member is provided in plural in a direction orthogonal to the conveyance direction of a sheet, and the contact state detecting part is provided corresponding to each contact member.

18. The method according to claim 16, wherein the print state determined by the print state determining part is a print rate representing the degree of an image portion occupying the whole sheet.

19. The method according to claim 16, wherein the print state determined by the print state determining part is the area of an image portion in the whole sheet.

20. The method according to claim 16, wherein the contact member is a conveyance guide that contacts with the surface of a sheet and guides the conveyance of the sheet.

* * * * *